(12) United States Patent
Picard et al.

(10) Patent No.: US 7,373,258 B2
(45) Date of Patent: May 13, 2008

(54) METHOD FOR MONITORING AND REGULATING SELECTIVE HYDROGENATION OF OLEFINIC GASOLINE FRACTIONS

(75) Inventors: Florent Picard, Communay (FR); Clementina Lopez Garcia, Lyons (FR); Jean-Marc Bader, Taluyers (FR); François Wahl, Champonost (FR)

(73) Assignee: Institute Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 11/592,329

(22) Filed: Nov. 3, 2006

(65) Prior Publication Data

US 2007/0103669 A1 May 10, 2007

(30) Foreign Application Priority Data

Nov. 4, 2005 (FR) .................................. 05 11277

(51) Int. Cl.
G06F 19/00 (2006.01)
(52) U.S. Cl. ........................... 702/28; 702/30; 702/75; 702/77
(58) Field of Classification Search ................. 702/27, 702/28, 30, 32, 85, 75, 77; 324/307, 310, 324/312; 250/339.07–339.09; 356/300, 356/303, 326; 326/300, 303
See application file for complete search history.

(56) References Cited

U.S. PATENT DOCUMENTS 4,277,315 A * 7/1981 Volkamer et al. ............. 203/51

| | | | |
|---|---|---|---|
| 5,452,232 A | | 9/1995 | Espinosa et al. |
| 5,712,481 A | * | 1/1998 | Welch et al. .......... 250/339.12 |
| 5,933,792 A | * | 8/1999 | Andersen et al. ............. 702/32 |
| 6,070,128 A | | 5/2000 | Descales et al. |
| 6,281,499 B1 | | 8/2001 | Kobayashi et al. |
| 2003/0212220 A1 | * | 11/2003 | Laubry ....................... 526/153 |

FOREIGN PATENT DOCUMENTS

| EP | 0 801 299 A | 10/1997 |
|---|---|---|
| FR | 2 619 625 A | 2/1989 |
| WO | WO 97/14951 A | 4/1997 |

OTHER PUBLICATIONS

Al-Douseri et al., 'Applications of THz-Time Domain Spectroscopy and Far-Infrared Fourier Transform Spectroscopy on Petroleum Product Analysis', 2004, IEEE Publicaiton, pp. 401-402.*
Takahashi, 'A Method for Learning the Varying Parameters of Gasoline Engine Control System Based on Detal Rule', 1996, IEEE Publication, pp. 2763-2768.*
Zanier-Szydlowski N. et al., Control of Refining Processes On Mid-Distillates By Near Infrared Spectroscopy, Reveu De L' Institut Francais Du Petrol, vol. 54, No. 4, Jul. 1999, pp. 463-472.

* cited by examiner

*Primary Examiner*—Edward Raymond
*Assistant Examiner*—Elias Desta
(74) *Attorney, Agent, or Firm*—Millen, White, Zelano & Branigan, P.C.

(57) ABSTRACT

This invention describes a method for determining the content of conjugated diolefins by means of the measurement of the MAV of a sample of catalytic cracking gasoline or thermal cracking gasoline, from its NIR (near-infrared) spectrum, and the application of said method for monitoring a unit for selective hydrogenation of the cracking gasolines.

13 Claims, 1 Drawing Sheet

Figure 1:
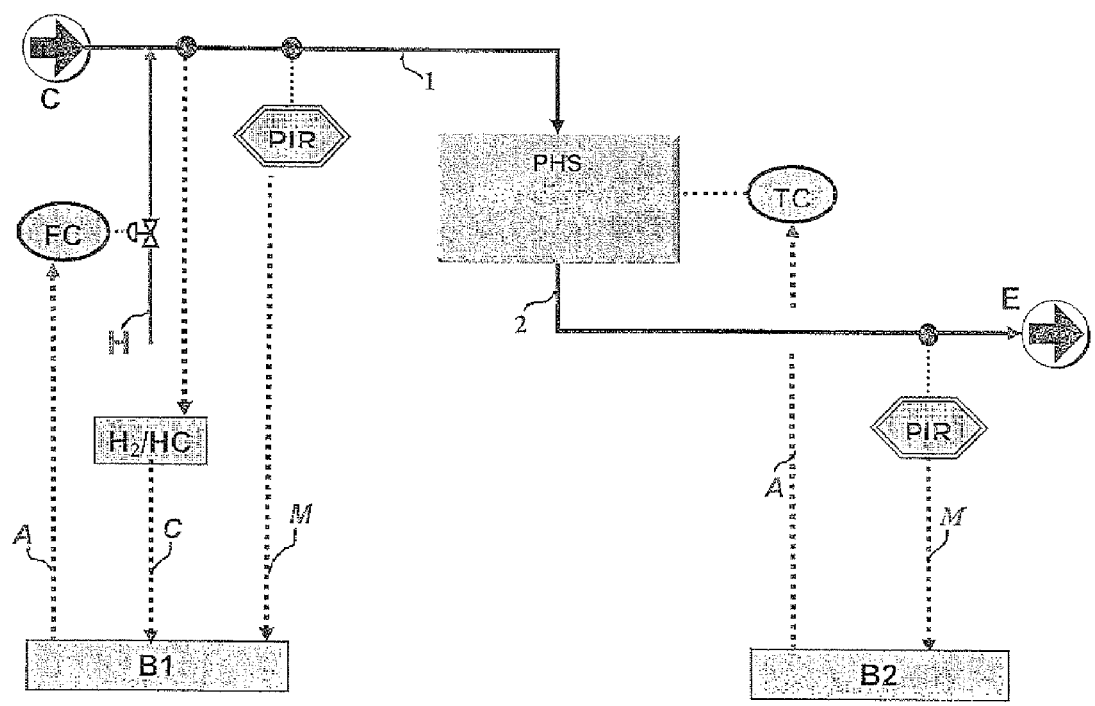

METHOD FOR MONITORING AND REGULATING SELECTIVE HYDROGENATION OF OLEFINIC GASOLINE FRACTIONS

FIELD OF THE INVENTION

The invention relates to the range of methods for determining various properties of hydrocarbon fractions, in particular gasolines, and more particularly the catalytic cracking gasolines, the steam-cracking gasolines, the coking gasolines and their mixtures, from their spectrum that is obtained in the near-infrared (denoted NIR spectrum in abbreviated form). In general, this invention applies to gasolines that contain sulfur (between 10 ppm and 10,000 ppm), olefins (at least 5% by weight), and diolefins (at least 0.1% by weight). The final distillation point of these gasolines should be less than 300° C., and preferably 250° C.

The near-infrared range corresponds to wavelengths encompassed approximately between 800 nanometers and 2,500 nanometers (14,286 to 4,000 $cm^{-1}$). The properties that can be determined from the MR spectrum of the gasolines are very diverse, whereby the primary ones up to now are density, octane numbers (RON and MON), Reid vapor pressure (RVP), the ASTM distillations, and the content of chemical families (paraffins, aromatic compounds, naphthenes, olefins), i.a.

In this invention, the property of which there is question is the conjugated diolefin content.

This content is indirectly measured by chemical methods that employ the Diels-Alder reaction. The principle of the method is the stoichiometric addition of maleic anhydride to the conjugated diolefins that are contained in the sample. The known methods that use this reaction to determine the diene values (DV) are, for example, described in Laboratory Test Methods for Petroleum and its Products, Universal Oil Products Method No. 326-82, Universal Oil Products, Illinois, USA or by the determination of MAV, abbreviation of "maleic anhydride value".

In this patent, we will refer to the MAV, but other methods for measuring conjugated diolefins in the gasolines such as the DV are also concerned.

The MAV is expressed in terms of the number of milligrams of maleic anhydride that react with a gram of a sample. This measurement is proportional to the content of conjugated diolefins present in the analyzed sample.

The determination of the conjugated diolefin content of a gasoline sample by chemical analysis according to the Diels-Alder reaction is a relatively long operation, on the order of 5 to 7 hours per analysis. In addition, this analysis is potentially dangerous because it requires the heating of the mixture of a solvent such as toluene with gasoline, and the manipulation of other solvents such as ethers.

The determination of the conjugated diolefin content by the Diels-Alder method is optionally used to measure the performance levels of the industrial units for selective hydrogenation of cracked gasolines, preferably gasolines that are obtained from catalytic cracking units, steam-cracking units and coking units. However, because of the operations that are necessary to the analysis, such as liquid extractions or product transfers, it is inconceivable to automate the method to make of it a method for continuous monitoring of the industrial units for selective hydrogenation.

One of the objects of this invention is to present a new method for determining the conjugated diolefin content in the gasolines by means of the measurement of the MAV or the variation of the MAV from the NIR spectrum, both faster and more repeatable than the method for determination by chemical analysis, and to use said new method in a chain for monitoring and regulating industrial units for selective hydrogenation of gasolines.

EXAMINATION OF THE PRIOR ART

The prior art is represented by patents and various communications that describe methods for determining a great variety of properties, such as density, octane numbers (RON and MON), Reid vapor pressure (RVP), the ASTM distillations, the content of chemical families (paraffins, aromatic compounds, naphthenes, olefins), and the MAV from an NIR spectrum.

Among the patents of this field, it is possible to consider the Patent U.S. Pat. No. 6,070,128 [2000] as describing the closest state of the art from the standpoint of the method itself.

This patent describes a method for determination of a property P of a hydrocarbon fraction that makes use of the absorption of a sample of the fraction being considered in a wavelength zone of between 600 and 2,600 nanometers (16,667 to 3,847 $cm^{-1}$) that consists in comparing the spectrum that is obtained with the spectra of a certain number of samples forming a base for which the property P is known.

The property P of the sample being considered is obtained by a so-called topology method. As will be disclosed in detail later, the method that is used in this invention for determining the property P from the NIR spectrum, in this case the MAV, is substantially different from the method disclosed in the cited Patent U.S. Pat. No. 6,070,128 since the idea of a spectrum difference between the spectrum of a sample that is used as reference and the spectra of other basic elements is used.

The result is a level of precision in the prediction of the MAV that is not accessible with a method that rests on the direct comparison of the spectra of the sample studied with the spectra of the elements of a known base with property P.

Regarding the methods for monitoring and regulating industrial units for selective hydrogenation, one skilled in the art knows a method that consists in tracking the temperature of the catalytic bed(s) at the input or the output and in using the temperature difference between the input and the output of the bed(s) as a monitoring parameter, i.e., in setting a maximum permissible delta T value from which one of the input parameters of the unit, most often the amount of hydrogen introduced, is to be modified.

The value of the amount of hydrogen introduced into the unit is determined from a ratio that is arbitrarily set relative to the flow rate of the entering feedstock, and a certain excess relative to the amount of hydrogen consumed by the reactions for selective hydrogenation of the diolefins and olefins.

The measurement of the MAV therefore is done only to monitor the adjustments of the unit a posteriori, but in no way for ensuring continuous adjustment of the parameters of the unit.

One of the contributions of the method described in this invention is to introduce continuous and rapid measurement of the diolefin content of the gasoline to be treated (called feedstock) and the treated gasoline (called effluent) for the purpose of determining the amount of hydrogen to be introduced into the unit to be continuously close to the stoichiometry.

Another application of the continuous measurement of the MAV is to make possible the adjustment of the temperature of the reactor(s) to ensure a conversion of the diolefins that is as close as possible to the target set by the operator.

The fact of being continuously close to the stoichiometry has a significant impact on the amount of hydrogen consumed and therefore on the economy of the process.

SUMMARY DESCRIPTION OF THE FIGURES

FIG. 1 shows a diagrammatic view of a unit for selective hydrogenation denoted PHS in which is shown the system for monitoring and regulating the object of the invention in the form of two loops, denoted B1 for the first loop and B2 for the second loop.

The meaning of the notations appearing in FIG. 1 is as follows:

A: Action
M: Measurement
C: Setpoint
FC: Flow Control
TC: Temperature Control
NIR: Near-Infrared Measurement
H2/HC: Ratio of the Hydrogen Flow Rate to the Feedstock Flow Rate The hydrocarbon feedstock that is to be treated (C) is introduced into the unit for selective hydrogenation (PHS) via the line (1), from which the hydrogenated effluent (E) is extracted via the line (2).

The other elements of FIG. 1 are described in detail in the detailed description of the invention.

SUMMARY DESCRIPTION OF THE INVENTION

The following description is provided with reference to the MAV, but the invention applies to any method for chemical determination of the diolefin content in cracking gasolines.

The MAV is a method for measurement of the conjugated diolefins that are present in a gasoline, based on the stoichiometric addition of diolefins to the maleic anhydride. It is expressed in terms of the number of milligrams of maleic anhydride that has reacted on one gram of the sample.

The method that is described in this invention is a method for determining the MAV of catalytic cracking gasoline or of pyrolysis gasoline or of coking gasoline or of any mixture of said gasolines, from the absorption spectrum obtained in the near-infrared (NIR) of the gasoline or said mixture, i.e., in a wavelength range encompassed between 800 and 2,500 nanometers.

The method for obtaining the MAV by NIR spectrum uses a comparison according to a specific criterion between the spectrum of the sample being studied and the spectra of a set of elements forming a base called a calibration base.

The calibration base consists of a set of N samples for each of which both the NIR spectrum and the value of the MAV, determined by the chemical method, are known.

The correlation between the MAV and the NIR spectrum is created from pairs of NIR/MAV spectrum values for each of the elements of the base. More specifically, the correlation is created from differences between the spectra of elements of the base, whereby an element of the base is selected as a reference element, and the differences between the values of the MAV for the sample being studied and for the reference sample.

This point is very important because it makes it possible to eliminate differences in the value of the MAV due to the chemical families that vary very little during the selective hydrogenation process (essentially paraffins, naphthenes, aromatic compounds and monoolefins) so as to bring out selectively the differences of the MAV that are due specifically to the variation of the diolefins.

The method consists in using an unknown series of MAV samples, taken at the input or at the output of the unit, and in forming the differences between these samples relative to a sample of the series that is taken as reference. To form the differences between samples means to create the difference between the spectra of said samples relative to a reference sample taken inside the series.

The difference of the spectrum is used to enter into the NIR correlation obtained from the calibration base and makes it possible to recover a MAV difference value.

Knowing the value of the MAV of the sample taken in reference, determined chemically, it then is possible to derive therefrom the value of the MAV for the other samples of the series.

The method that will be called "delta" method below comprises the following stages:

a) A sample taken in a series that will be used as a reference sample is selected,
b) The NIR spectrum as well as the MAV are determined by the chemical method of the reference sample,
c) The NIR spectrum is determined from the other elements of the series,
d) The difference between the spectrum of the reference sample and that of a sample of the series of which the MAV is unknown is calculated, whereby this spectrum difference is called a subtracted spectrum,
e) It is verified that the subtracted spectrum is inside the range of the NIR model,
f) A variation value of the MAV is calculated from the subtracted spectrum by using the correlation obtained from the calibration base,
g) The MAV of the sample being studied is calculated from the MAV variation obtained in stage f) and the chemical MAV of the reference sample.

This sample can be used sequentially or continuously.

The application of the method for monitoring and regulating the units for selective hydrogenation is done by two regulation loops, denoted loop 1 (or input loop) and loop 2 (or output loop), which will be disclosed in detail later.

The determination of the MAV of the feedstock, on the one hand, and the effluent, on the other hand, is carried out from a series of samples taken over time according to the method described above, whereby the reference sample is generally the first sample obtained over time.

The frequency of sampling is generally one sample per hour, and preferably one sample per half-hour.

To simplify, below input MAV will be called the MAV of the feedstock determined by the "delta" method, and output MAV will be called the MAV of the effluent determined by the "delta" method.

The two regulation loops operate in a simultaneous and independent manner. More specifically, the method that is described in this invention is a method for monitoring and regulating units for selective hydrogenation of olefinic gasoline fractions that consist in the sequence of following stages:

A sample is taken at the input and at the output of said unit at a determined frequency, Said samples are analyzed by their NIR spectrum by absorption in a wavelength range of between 800 nm and 2,500 nm, The $MAV_{NIR}$ of the input and output samples is determined by a treatment of the NIR spectra using a calibration base and a specific pretreatment, The amount of hydrogen to be introduced into the unit that is used as a setpoint value in a first regulation loop of said value of the $MAV_{NIR}$ as input is determined from the $MAV_{NIR}$ of the input sample and the flow rate of the feedstock, The optimum input temperature in the reactor that is used as a setpoint value in a second regulation loop of said value of the $MAV_{NIR}$ as output is determined from the $MAV_{NIR}$ of the output sample and a dynamic model.

The method for monitoring and regulating industrial units for selective hydrogenation of olefinic gasoline fractions according to the invention therefore requires taking samples at the input and the output of the unit, with a sampling frequency of said samples of one sample per hour and preferably one sample per half-hour.

The set of the input and output samples taken over time forms a series.

The determination of the MAV of each sample i of a series uses a method by subtraction of spectra, a so-called delta method, characterized by the sequence of the following operations:

A series of samples are taken at the input or the output of the unit for selective hydrogenation at a determined frequency, A reference sample is selected inside the series of samples for which the MAV is determined chemically, The NIR spectra of each sample i of the series are obtained, The spectrum difference is formed between the spectrum of each sample i and the spectrum of the reference sample, The $Delta_{13}$ MAV of each sample is derived from the spectrum difference of said sample i with the spectrum of the reference sample by using a correlation that is obtained from a calibration base, The MAV of sample i is obtained from the Delta_MAV of the sample i and the MAV of the reference sample.

The method for monitoring and regulating industrial units for selective hydrogenation of olefinic gasoline fractions according to the invention requires a calibration base that consists of at least n samples taken from the feedstock or from the effluent, or, preferably, composed of elements taken from the feedstock and other elements taken from the effluent. The number of samples n is greater than 20, and preferably greater than 30.

Generally, the calibration base is not fixed, and it is possible to add elements to it over time that make it possible to broaden its field of application.

The method for monitoring and regulating industrial units for selective hydrogenation of olefinic gasoline fractions according to the invention makes it possible to produce gasolines whose diolefin content is optimum for limiting both the deactivation speed of the catalyst for selective hydrogenation as well as the premature ageing of catalysts contained in the units for treatment of the gasoline that are located downstream from the selective hydrogenation.

Actually, an excessive diolefin content of the effluent could lead to a premature deactivation of the catalysts used in the treatments downstream from the selective hydrogenation by an increased deposition of polymers.

DETAILED DESCRIPTION OF THE INVENTION

This invention is a method for monitoring and regulating units for selective hydrogenation of olefinic gasolines, as they are encountered in the processes for desulfurization of the catalytic cracking gasolines, pyrolysis gasolines, coking gasolines or mixtures thereof.

In general, it is possible to characterize the gasolines to which this invention applies by their sulfur content of between 10 ppm and 10,000 ppm, their olefin content of at least 5% by weight, their diolefin content of at least 0.1% by weight, and by their distillation interval of between 40° C. and 300° C., and preferably between 40° C. and 250° C.

This invention actually applies to any unit for selective hydrogenation of gasolines requiring a high precision in the hydrogenation rate.

In the context of the processes for desulfurization of the catalytic cracking gasolines, it is essential to limit the hydrogenation to diolefin-type compounds that are responsible for the formation of gums that can obstruct the units downstream, without going as far as hydrogenating monoolefins that contribute to the good value of the octane number of the gasoline that is produced.

The monitoring of the units for selective hydrogenation is commonly carried out by means of a regulation loop that focuses on the monitoring of the amount of hydrogen introduced into the unit. This amount of hydrogen is defined relative to the amount that is necessary for the hydrogenation of diolefins (called stoichiometric amount) by adding a certain excess to it.

In this invention, the monitoring of the units for selective hydrogenation is done from a measurement of the MAV at the input and at the output of the unit, each of these two measurements being used to develop a setpoint value respectively for an input regulation loop and an output regulation loop.

The first regulation loop, or input loop, monitors the flow rate of hydrogen at the input by acting on the amount of hydrogen to be introduced into the unit from the measurement of the MAV of the feedstock, and the second loop, or output loop, monitors the MAV of the effluent by acting on the input temperature of the reactor for selective hydrogenation.

If the unit has several reactors for selective hydrogenation that operate in a series, each of them, or at least the first and the last reactor of the series, are the object of the system for monitoring and regulation according to this invention.

In the text below, there are described in a detailed manner:
1) The method for obtaining the MAV from the NIR spectrum,
2) The regulation loop of the input MAV,
3) The regulation loop of the output MAV.

1) Method for Obtaining the MAV from the Near-Infrared Spectrum ($MAV_{NIR}$)

The method for obtaining the MAV from the NIR spectrum, or in abbreviated modeling NIR, consists in correlating the spectra that are obtained in the near-infrared (NIR) range with one or more properties of a sample base called a calibration base. Below, the expressions "obtain the MAV from the NIR spectrum" or "model the MAV by NIR" will be used equally.

Any new sample of which it is sought to determine the property P from its NIR spectrum is compared to the so-called calibration base, and the property P is only calculated by the correlation if the new sample is within the range covered by the calibration base.

The correlations between spectra and properties are developed with statistical analysis methods that are known in the literature, for example the one that is defined by Martens, H.; Naes, T. "Multivariate Calibration" Ed. John Wiley & Sons, Great Britain, 1991. These statistical methods are, for example, the multiple linear regression (MLR or multilinear regression, in English), the regression by primary components (PCR or principal component regression, in English), or the so-called method of partial least squares (PLS or partial least squares, in English).

The MAV of the output gasolines of the industrial units for selective hydrogenation can reach very low values that are generally less than or equal to 2 milligrams/gram.

These values of the MAV are equivalent to conjugated diolefin contents that are less than 0.3% by weight in the gasolines.

Now, the limit commonly used to model properties by NIR is about 1% by weight.

The prediction of the conjugated diolefin content for the output gasolines for selective hydrogenation is therefore difficult to carry out by the standard techniques of NIR modeling because the absorption bands of the olefins interfere with those of the diolefins. In addition, the diolefins are present in a very low content in the samples.

In addition, the absorption bands of the spectra primarily represent the majority hydrocarbons that are present in the gasolines (paraffins, aromatic compounds, naphthenes, olefins) and in a very small proportion the conjugated diolefins. Thus, the standard models that are developed from raw spectra data are very hard to apply to the determination of the MAV of the gasolines, in particular at the output of the units for selective hydrogenation.

This invention describes a method for treatment of NIR spectra that makes possible the prediction of the MAV in the context of the process for selective hydrogenation of the gasolines.

In the process for selective hydrogenation of the catalytic cracking gasolines or thermal gasolines, the differences in chemical composition of the effluents over time are for the most part due to the variation of the conjugated diolefin content and the weak hydrogenation of the olefins.

From this finding, instead of directly modeling the MAV, the method of this invention proposes the modeling of the variation of the MAV between a reference sample and a sample that is obtained from the input or output process, designated in the text below by "sample i." The sample i is an effluent of unknown MAV of which the MAV is determined sequentially or continuously by the variation method of the MAV, so-called "delta" method.

The variation of the NIR-calculated MAV is designated as the Delta$_{\_MAVNIR}$ and is calculated as Delta$_{\_MAVNIR\ i}$= MAV$_{reference}$−MAV$_{NIR\ i}$.

The reference sample can be either a sample of a series taken from the input feedstock or a sample of a series taken from the effluent of the process.

The MAV of the reference sample is to be determined by the chemical method.

If the Delta_MAV$_{NIR}$ of the effluent i is calculated by the NIR model, the unknown MAV of this sample can be calculated by the difference MAV$_{NIR\ i}$=MAV$_{reference}$−Delta_ MAV$_{NIR\ i}$.

The stages that make it possible to obtain the MAV values by near-infrared (designated MAV$_{NIR}$) of the gasolines that are obtained from the units for selective hydrogenation are described below:

Obtaining Samples:

The samples are catalytic cracking gasolines or thermal cracking gasolines that are taken from the input or from the output of the unit for selective hydrogenation of the so-called olefinic gasolines. "Series" designates a set of samples taken from the input or from the output of the unit.

A sample of the series should be selected as a reference. In general, the reference sample is the first in the chronological order of taking samples from said series.

The NIR analysis can be carried out with or without sampling (relocation, on-line, or by any other means of deriving the sample). Preferably, the NIR analysis will be carried out without sampling.

If the feedstock of the unit is modified, it may be useful to select a new reference sample both in an input series and in an output series.

This operation should be carried out once the unit is under stabilized conditions to prevent the taking of samples corresponding to mixtures of different feedstocks, as can happen under temporary conditions.

When the unit is operating, the frequency of taking samples is limited by the treatment period of the NIR spectrum. In general, a frequency of taking one sample per hour or per half-hour is easily feasible. This frequency can be higher, if necessary.

Analysis of the Samples:
The analysis of the samples consists of 2 primary stages:
Determination of the MAV chemically for the reference sample.
Determination of the NIR spectra of the samples of the series. The NIR spectra should be recorded in transmission mode in a wavelength range of between 800 nm and 2,500 nm. The spectra should be determined only in liquid fractions of the gasolines.

Pretreatment of the NIR Spectra:

The spectra should be subjected to standard pretreatments commonly practiced for the modeling of properties by NIR. These pretreatments are known and described in the literature [Martens et al.]. This invention uses a pretreatment that consists in correcting the base line of the spectra between the wavelengths affected by the NIR model.

After this first pretreatment, the difference in spectra between the reference sample of the series and any sample i of said series is calculated according to equation 1.

$$A_{diff_{ref-ik}} = (A_{ref_k} - A_{ik})|  \quad \text{Equation 1}$$

where $A_{diff_{ref-ik}}$ is the difference in absorbance between the reference sample and a sample i with the wavelength k, $A_{ref_k}$ is the absorbance of the reference sample with the wavelength k, $A_{ik}$ is the absorbance of the sample i.

Equation 1 is applied with k=1 to K wavelengths concerned in the NIR model.

Equation 1 is applied to all the samples i forming the series for which the MAV is unknown.

It is verified that each sample i belongs to the samples that form the calibration base.

This verification of belonging makes it possible to determine if the NIR model can be applied to each sample i of the series studied. This verification of belonging consists of a series of tests known to one skilled in the art.

Among the standard tests of belonging, it is possible to cite the calculation of the influence of the sample i on the NIR model. The influence consists in calculating the weight of the sample i in the NIR model and its residual variance. These tests are of the public domain and are described in the literature [for example, Martens et al.].

Determination of the MAV of Sample i:

The Delta_$MAV_{NIR}$ property of each sample that passes the test of belonging of the preceding paragraph may be calculated from the NIR model created from a calibration base for which the differences of spectra and their corresponding Delta_$MAV_{NIR}$ are known.

The $MAV_{NIR}$ of each sample of which the Delta_$MAV_{NIR}$ is known can be calculated from Equation 2:

$$MAV_{PIR_i} = MAV_{ref} - Delta\_MAV_{PIR_i} \qquad \text{Equation 2}$$

where:

$MAV_{PIR_i}$ is the MAV of the sample i of the series that is calculated by NIR in mg/g,

[Key: PIR=NIR]

$MAV_{ref}$ is the MAV by chemical means of the reference sample of the series in mg/g, Delta_$MAV_{NIRi}$ is the result of the NIR model for the sample i in mg/g.

The previously described stages are valid for calculating the $MAV_{NIR}$ for the monitoring of the unit provided that the feedstock at the input of the process remains constant. If the feedstock at the input of the unit changes, a new reference sample is to be sampled and analyzed. The corresponding data in the calculations of equations 1 and 2 should then consequently be modified.

2) Description of the First Regulation Loop of the Input MAV (B1)

The following description is given with reference to FIG. 1.

A correlative calculation, based on a kinetic model of the reaction, makes it possible to determine, in an open loop, the optimum H$_2$/HC ratio in which the reaction should take place. This correlative calculation uses the value of the input MAV that is calculated from successive samples of the feedstock. Each of the samples taken from the feedstock provides an NIR spectrum from which the MAV is derived according to the delta method described in the preceding paragraph. It is advisable to note that this correlative calculation can be applied regardless of the kinetic model used to show the chemical reaction of hydrogenation.

An advanced monitoring loop (B1) then controls the setpoint of the flow meter of hydrogen by taking into consideration the H$_2$/HC setpoint that is developed by the correlative calculation, and the measurement of H$_2$/HC that is itself based on the measurement of the feedstock flow rate and the H$_2$ flow rate.

The regulation loop implemented by the flow controller (FC) therefore automatically makes it possible to regulate the hydrogen flow rate so as to be at each instant close to the setpoint value denoted H2/HC.

The line C diagrammatically shows the development of the H2/HC setpoint.

The line M diagrammatically shows the measurement of the diolefin content of the so-called $MAV_{NIR}$ feedstock obtained from the NIR spectrum of the sample being considered according to the delta method.

The line A designates the automatic regulation action of the hydrogen flow rate by means of the flow controller (FC).

This invention therefore uses a first regulation loop or input loop that monitors the flow rate of hydrogen to be introduced into the unit from the measurement of the $MAV_{NIR}$ of the feedstock that makes it possible to develop the setpoint value of the H2/HC ratio.

3) Description of the Second Regulation Loop of the Output MAV (B2).

The following description is provided with reference to FIG. 1.

An advanced monitoring loop (B2) adjusts the setpoint of the input temperature of the reactor so as to carry out, under the best conditions, the desired degree of hydrogenation of the diolefins.

A dynamic model (locked in real time) between the input temperature of the reactor and the MAV of the effluent is used for the calculation of the actions of modification of said input temperature.

This dynamic model can be seen as a correspondence created over time between the input temperature of the reactor and the $MAV_{NIR}$ of the effluent obtained from the NIR spectrum of effluent samples of a given series. By using this correspondence, it is therefore possible to transform a setpoint of diolefin content in the effluent into an input temperature setpoint of the reactor.

The line M diagrammatically shows the measurement of the diolefin content of the output sample, or $MAV_{NIR}$ of the effluent, obtained from its NIR spectrum according to the delta method disclosed in the preceding paragraph.

The line A diagrammatically shows the automatic regulation action carried out by the temperature controller (TC) from the measurement M and the setpoint value of the input temperature of the reactor calculated from a dynamic model.

The method for monitoring and regulating industrial units for selective hydrogenation of olefinic gasoline fractions according to the invention therefore uses a second regulation loop or an output loop that monitors the input temperature of the reactor from a setpoint developed from the $MAV_{NIR}$ of the effluent, whereby said $MAV_{NIR}$ is determined in an output series of samples of the unit from their NIR spectrum according to the delta method.

EXAMPLE ACCORDING TO THE INVENTION

In this example, three olefinic gasolines, whose characteristics are provided in Table 1 below, are treated in a unit for selective hydrogenation working with a catalyst based on nickel and molybdenum.

The values of the temperature at the input of the reactor and the non-dimensional H2/HC ratio (HC designating the feedstock) are provided here purely by way of illustration and do not at all limit the scope of the invention that applies to every unit for selective hydrogenation of olefinic gasolines.

Three series of samples, corresponding to each of the treated feedstocks, have been taken from the output of the unit for selective hydrogenation of olefinic gasoline at a frequency of one sample every half-hour.

These effluents correspond to the different operating conditions of the unit for selective hydrogenation restated in Table 2.

The $MAV_{NIR}$ values of the samples were calculated via the "Delta_$MAV_{NIR}$" method.

The unit using an on-line analyzer, the NIR measurement was able to be carried out in real time and thus avoids exceeding the target MAV (2 mg/g) at the output of the unit thanks to the two regulation loops proposed in this invention, as described in the detailed description.

Table 2 below compares the values of the $MAV_{NIR}$ determined according to the delta method in the 3 series of samples, with the values of the chemical MAV. The agreement between the 2 value series is remarkable and allows a very fine control of the unit by means of the 2 regulation loops described in the text.

TABLE 1

Global Characteristics of the Feedstocks of Each Series.

| | | Series 1 | Series 2 | Series 3 |
|---|---|---|---|---|
| Density at 15° C. | g/cm³ | 0.779 | 0.738 | 0.772 |
| Sulfur | ppm by Weight | 2580 | 1260 | 3480 |
| Simulated Distillation 5% | ° C. | 23 | 23 | 23 |
| Simulated Distillation 50% | ° C. | 140 | 92 | 126 |
| Simulated Distillation 95% | ° C. | 217 | 183 | 233 |
| MAV | mg/g | 13.0 | 9.9 | 17 |
| Paraffins | % by Weight | 22 | 31 | 22 |
| Olefins | % by Weight | 31 | 34 | 36 |
| Naphthenes | % by Weight | 6 | 8 | 6 |
| Aromatic Compounds | % by Weight | 41 | 27 | 36 |

TABLE 2

Compared Values of the Chemical MAV and According to the NIR Delta Method for Different Operating Conditions from the Unit for Selective Hydrogenation

| | No. of the Sample of the Series | $MAV_{chemical}$ (mg/g) | $MAV_{NIR}$ (mg/g) | Temperature e (° C.) | H2/HC |
|---|---|---|---|---|---|
| Series 1 | 1 | 1.8 | 1.9 | 170 | 25 |
| | 2 | 1.5 | 1.7 | 170 | 25 |
| | 3 | 5.8 | 6.2 | 170 | 20 |
| Series 2 | 1 | 5.4 | 5.4 | 150 | 25 |
| | 2 | 2.8 | 3.2 | 150 | 20 |
| | 3 | 2.5 | 2.6 | 150 | 25 |
| | 4 | 6.7 | 6.6 | 140 | 25 |
| | 5 | 3.5 | 3.7 | 150 | 25 |
| | 6 | 0.7 | 0.6 | 170 | 25 |
| | 7 | 0.9 | 0.9 | 150 | 25 |
| | 8 | 0.5 | 0.9 | 150 | 25 |
| Series 3 | 1 | 5.9 | 6.4 | 140 | 20 |
| | 2 | 3.7 | 3.5 | 150 | 20 |
| | 3 | 7.6 | 8.2 | 140 | 20 |
| | 4 | 3.5 | 3.2 | 170 | 20 |
| | 5 | 8.6 | 8.5 | 140 | 20 |

The preceding examples can be repeated with similar success by substituting the generically or specifically described reactants and/or operating conditions of this invention for those used in the preceding examples.

The entire disclosures of all applications, patents and publications, cited herein and of corresponding French application No. 05/11.277, filed Nov. 4, 2005 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for monitoring and regulating a reactor for selective hydrogenation of an olefinic gasoline fraction feedstock containing a conjugated diolefin content, said feedstock flowing at a measured rate into said reactor, said method comprising adjusting the temperature of the reactor and hydrogen input to the reactor in response to maleic anhydride value (MAV) from samples taken at the input and the output of the reactor obtained by conducting the following sequence of stages:

Withdrawing a sample at the input and at the output of said reactor at a determined frequency, Analyzing samples by their near infrared (NIR) spectrum by absorption at a wavelength range of between 800 nm and 2500 nm, Determining the maleic anhydride value ($MAV_{NIR}$) by near infrared values of the input and output samples determined by a treatment of the NIR spectra using a calibration base and a specific treatment, Determining from the $MAV_{NIR}$ of the input sample and the flow rate of the feedstock the amount of hydrogen to be introduced into the reactor that is used as a set point value in a first regulation loop of said value of the $MAV_{NIR}$ as input, Determining an optimum input temperature in the reactor that is used as a set point value in a second regulation loop of said value of the $MAV_{NIR}$ as output is determined from the $MAV_{NIR}$ of the output sample and a dynamic model, and in which the determination of MAV of each sample i of a series is conducted by a subtraction of spectra (delta method), characterized by the following sequence of operations:

A series of samples is taken at the input or the output of the reactor for selective hydrogenation at a determined frequency, A reference sample is selected from an intermediate sample in the series of samples for which the MAV is determined chemically, The NIR spectra of each sample i of the series are obtained, The spectrum difference is formed between the spectrum of each sample i and the spectrum of the reference sample, The delta MAV of each sample is derived from the spectrum difference of said sample i with the spectrum of the reference sample by using correlation that is obtained from the calibration base, The MAV of sample i is obtained from the delta MAV of the sample i and the MAV of the reference sample.

2. A method for monitoring and regulating a reactor for selective hydrogenation of olefinic gasoline fractions according to claim 1 in which the frequency of taking input and output samples is at least one sample per hour.

3. A method for monitoring and regulating a reactor for selective hydrogenation of olefinic gasoline fractions according to claim 1, in which the calibration base consists of at least n samples taken both from the feedstock and from the effluent, whereby n is greater than 20.

4. A method for monitoring and regulating a reactor for selective hydrogenation of olefinic gasoline fractions according to claim 1, in which the calibration base is composed of at least n samples taken both from the feedstock and from the effluent wherein n is greater than 30.

5. A method for monitoring and regulating a reactor for selective hydrogenation of olefinic gasoline fractions according to claim 1, in which the input regulation loop uses a correlative calculation, based on a kinetic model of the reaction, making it possible to determine in an open loop the optimum $H_2/HC$ ratio in which the reaction should take place, whereby said correlative calculation uses the value of the input MAV calculated on a series of samples of the feedstock from their NIR spectrum according to the delta method.

6. A method for monitoring and regulating a reactor for selective hydrogenation of olefinic gasoline fractions according to claim 1, in which the output regulation loop uses as a setpoint the input temperature of the reactor and a dynamic model locked in real time from the input temperature of the reactor and the MAV of the effluent, whereby said MAV is determined on a series of output samples of the unit from their NIR spectrum according to the delta method.

7. A method for monitoring and regulating a reactor for selective hydrogenation of olefinic gasoline fractions according to claim 1, in which the value of the MAV of the output gasolines of said industrial units is less than or equal to 2 milligrams per gram.

8. A method for monitoring and regulating a reactor for selective hydrogenation of olefinic gasoline fractions according to claim 3 in which the frequency of taking input and output samples is at least one sample per hour.

9. A method for monitoring and regulating a reactor for selective hydrogenation of olefinic gasoline fractions according to claim 4 in which the frequency of taking input and output samples is at least one sample per hour.

10. A method for monitoring and regulating a reactor for selective hydrogenation of olefinic gasoline fractions according to claim 5 in which the frequency of taking input and output samples is at least one sample per hour.

11. A method for monitoring and regulating a reactor for selective hydrogenation of olefinic gasoline fractions according to claim 6 in which the frequency of taking input and output samples is at least one sample per hour.

12. A method for monitoring and regulating a reactor for selective hydrogenation of olefinic gasoline fractions according to claim 7 in which the frequency of taking input and output samples is at least one sample per hour.

13. A method for monitoring and regulating a reactor for selective hydrogenation of olefinic gasoline fractions according to claim 1 in which the frequency of taking input and output samples is at least one sample per half hour.

* * * * *

UNITED STATES PATENT AND TRADEMARK OFFICE
CERTIFICATE OF CORRECTION

PATENT NO. : 7,373,258 B2 Page 1 of 1
APPLICATION NO. : 11/592329
DATED : May 13, 2008
INVENTOR(S) : Florent Picard It is certified that error appears in the above-identified patent and that said Letters Patent is hereby corrected as shown below:

On the Title page Item (75), Inventors: line 2, reads "Lyons" should read --Lyon--
Column 12, line 25, begin new line after "dynamic model,"

Signed and Sealed this

Sixteenth Day of December, 2008

JON W. DUDAS
*Director of the United States Patent and Trademark Office*